United States Patent
McDonnell

[11] Patent Number: 6,126,688
[45] Date of Patent: Oct. 3, 2000

[54] APPARATUS FOR FUSION OF ADJACENT BONE STRUCTURES

[75] Inventor: Christopher McDonnell, Newtown, Conn.

[73] Assignee: Surgical Dynamics Inc., Norwalk, Conn.

[21] Appl. No.: 09/217,325

[22] Filed: Dec. 21, 1998

[51] Int. Cl.[7] ............................................. A61F 2/44
[52] U.S. Cl. ......................................................... 623/17.16
[58] Field of Search ................................. 433/173, 201.1; 623/16, 17, 17.16, 23.75; 606/60, 61, 62, 72, 77; 132/245, 226, 261

[56] References Cited

U.S. PATENT DOCUMENTS

| | | | |
|---|---|---|---|
| 3,623,164 | 11/1971 | Bokros | 606/63 |
| 4,437,191 | 3/1984 | Van Der Zel et al. | 623/16 |
| 4,792,336 | 12/1988 | Hlavacek et al. | 623/13 |
| 4,834,757 | 5/1989 | Brantigan | 623/16 |
| 4,961,740 | 10/1990 | Ray et al. | 623/16 |
| 5,015,247 | 5/1991 | MIchelson | 623/17 |
| 5,618,286 | 4/1997 | Brinker | 606/60 |
| 5,645,598 | 7/1997 | Brosnahan, III | 623/17 |
| 5,702,449 | 12/1997 | McKay | 623/17.16 |
| 5,749,874 | 5/1998 | Schwartz | 606/77 |
| 5,785,710 | 7/1998 | Michelson | 623/17 |
| 5,972,368 | 10/1999 | McKay | 623/16 |

FOREIGN PATENT DOCUMENTS

| | | | |
|---|---|---|---|
| 4409836 | 9/1995 | Germany | 623/17.16 |
| 9838948 | 9/1998 | WIPO | 623/17.16 |

*Primary Examiner*—Gene Mancene
*Assistant Examiner*—Eduardo C. Robert

[57] ABSTRACT

A prosthetic implant apparatus for facilitating fusion of adjacent vertebral portions, includes an implant member dimensioned to be at least partially positioned within an intervertebral space defined between adjacent vertebral portions. The implant member includes a bioabsorbable material and has a support structure associated therewith. The support structure is sufficiently rigid to support and maintain the adjacent vertebral portions in spaced relation during healing.

18 Claims, 4 Drawing Sheets

APPARATUS FOR FUSION OF ADJACENT BONE STRUCTURES

BACKGROUND

1. Technical Field

The present disclosure relates generally to a surgical apparatus for fusing adjacent bone structures, and, more particularly, to an apparatus and method for fusing adjacent vertebrae.

2. Background of the Related Art

The fusion of adjacent bone structures is commonly performed to provide for long-term replacement to compensate for degenerative or deteriorated disorders in bone. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. For example, U.S. Pat. No. 4,887,020 to Vich discloses a cylindrical bone plug having a thread on its exterior, which is screwed into a correspondingly dimensioned cylindrical bore drilled in the intervertebral space. Other bone grafting plugs are disclosed in U.S. Pat. No. 4,950,296.

More recently, emphasis has been placed on fusing bone structures (i.e., adjoining vertebrae) with prosthetic cage implants. One fusion cage implant is disclosed in U.S. Pat. No. 5,026,373 to Ray et al. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a pre-defined intervertebral space. The adjacent vertebral bone structures communicate through the apertures with bone growth inducing substances within the internal cavity to unite and eventually form a solid fusion of the adjacent vertebrae. Other prosthetic implants are disclosed in U.S. Pat. Nos.: 4,501,269; 4,961,740; 5,015,247; and 5,489,307.

Fusion implants or cages of the type aforedescribed are typically made from a biocompatible rigid material such as titanium or titanium alloys, ceramics, stainless steel, etc. These implants become permanently fixed within the spinal column as a result of the fusion process to remain in the patient indefinitely.

Recent emphasis has been placed on the use of synthetic bioabsorbable polymers for the manufacture of implantable surgical devices such as surgical fasteners, clips, staples and sutures. An advantage of the bioabsorbable devices is that they degrade and are absorbed by the body over a period of time. Ideally, the bioabsorbable surgical device maintains its strength for as long as it takes the body tissue to heal and, thereafter, rapidly degrades and disappears.

SUMMARY

Accordingly, the present disclosure is directed to an apparatus for facilitating fusion of adjacent vertebral portions, which is fabricated, at least in part, of a bioabsorbable material to eliminate or reduce the volume of foreign implant matter left within the vertebral column. In one preferred embodiment, the apparatus includes an implant member dimensioned to be at least partially positioned within an intervertebral space defined between adjacent vertebral portions. The implant member includes a bioabsorbable material and has a sufficiently rigid support structure associated therewith. The bioabsorbable material and the support structure cooperate to support and maintain the adjacent vertebral portions in spaced relation during healing. Preferably, the bioabsorbable material is selected from a group consisting of polymers or copolymers of glycolide, lactide, troxanone, trimethylene carbonate and lactones.

The implant member defines an internal cavity for reception of bone growth inducing substances and may have a plurality of apertures extending through an outer wall thereof in communication with the internal cavity to permit bone ingrowth.

The support structure includes a material selected from the group consisting of stainless steel, titanium, titanium alloys, aluminum, polymeric material and ceramic. Preferably, the support structure is a cage structure having at least two axial rib portions and a plurality of peripheral rib portions connecting the axial rib portions. The implant member is at least partially disposed within an internal opening of the support structure.

Other preferred embodiments are also disclosed.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

The preferred embodiment(s) of the apparatus and method disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of the fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator, while the term "distal" will refer to the portion which is further from the operator.

Fusion Implant

Figure 1:
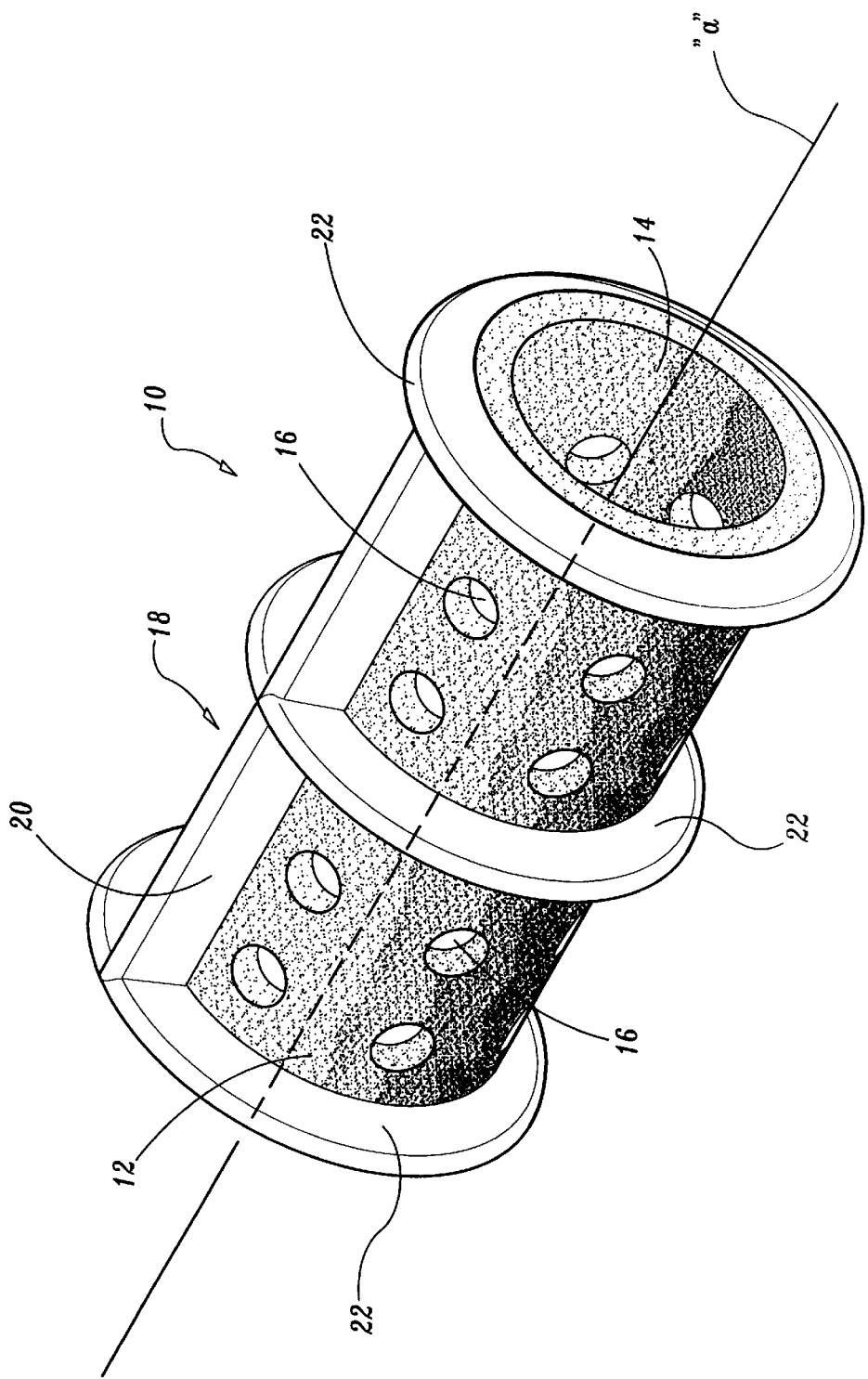
FIG. 1 is a perspective view of the apparatus in accordance with the principles of the present disclosure illustrating the bioabsorbable fusion implant and a support structure associated therewith.

Referring now to FIG. 1, the fusion implant of the present disclosure is illustrated. Implant 10 is preferably fabricated in part of a bioabsorbable polymeric material which over a period of time degrades to be absorbed by the patient thereby leaving minimal trace of the implant. Fusion implant 10 is intended to at least partially replace the supporting function of an intervertebral disc, i.e., to maintain adjacent vertebrae in desired spaced relation during healing and fusion. Preferably, two implants 10 are utilized and disposed on lateral sides of the intervertebral disc space. Implant 10 is preferably provided in various lengths such as from about 18–28 mm and in various cross-sectional dimensions to generally correspond to the spinal location to which it is to be implanted.

With specific reference to FIG. 1, the construction of the preferred embodiment of implant 10 will be discussed in detail. Fusion implant 10 includes implant member 12 which is fabricated from a bioabsorbable material. Suitable bioabsorbable materials include polymers or copolymers of glycolide, lactide, troxanone, trimethylene carbonate, lactones, etc. These materials may be manufactured to have various mechanical properties such as improved strength, impact resistance, etc. Preferably, implant member 12 is fabricated from a bioabsorbable material which provides sufficient rigidity to at least partially support the adjacent vertebral portions in spaced relation and which commences degradation after fusion of the adjacent vertebral portions begins. One skilled in the art and familiar with bioabsorbable materials and its properties may readily appreciate the bioabsorbable material composition to achieve these objectives.

Implant member 12 is generally cylindrically-shaped as shown. Implant member 12 defines longitudinal axis "a" extending the length of the implant member 12. Other shapes and dimensions are envisioned as well including elliptical-shaped, rectangular-shaped, etc. Implant member 12 is generally enclosed defining internal cavity 14 therein. Internal cavity 14 is dimensioned to accommodate bone growth inducing substances which may be packed within the cavity 14 to facilitate bone ingrowth and fusion. A plurality of apertures 16 extend through the outer wall of the member 12 in communication within the internal cavity 14. Apertures 16 permit bone ingrowth of the bone growth inducing substances within internal cavity 14 and the adjacent vertebral tissue portions. Apertures 16 are preferably substantially the same in dimension although it is envisioned that the dimensions of the apertures may vary to provide for more or less bone ingrowth.

Fusion implant 10 further includes support structure or strut 18 which provides support for bioabsorbable member 12 during the initial stages of healing and thereafter. Support structure 18 is, in the preferred embodiment, in the form of a cylindrical cage structure defining an internal bore to receive bioabsorbable member 12. Preferably, the internal bore of support structure 18 generally corresponds to the outer diameter of implant member 12 to form a frictional fit between the two components. Support structure 18 has first and second diametrically opposed axial support struts 20 (one is shown in FIG. 1) and a plurality, e.g. 3, of peripheral support ribs 22 connected to the support struts 20. Support struts 20 and support ribs 22 are advantageously dimensioned to engage the adjacent vertebral portions upon insertion and to maintain such portions in spaced relation during healing and while the bioabsorbable member is absorbed into the body. Support structure 18, and namely support ribs 22, will also initially bear most of the load, i.e. until fusion occurs between the bone graft and the vertebral bone. Support structure 18 is fabricated from a nonabsorbable biocompatible material. One preferred material is titanium or a titanium alloy which is highly suitable for human implantation. Other suitable materials include stainless steel, aluminum, polymeric material and/or ceramics.

Insertion of Fusion Implant

The insertion of the fusion implant 10 into an intervertebral space defined between adjacent lumbar vertebrae will now be described. The subsequent description will be particularly discussed in conjunction with an open approach for spinal fusion implant insertion, e.g., an open posterior or an open anterior, however, it is to be appreciated that other approaches, e.g., postero-lateral etc. are contemplated as well. Laparoscopic approaches are also envisioned.

Figure 2:
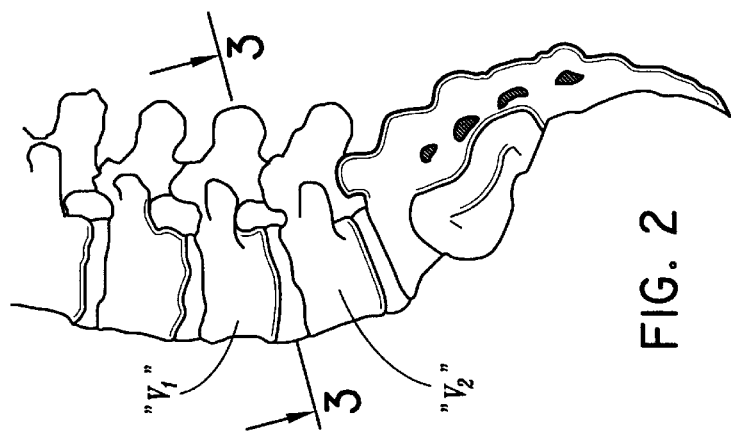
FIG. 2 is a view of a portion of the vertebral column illustrating the intervertebral space defined between adjacent vertebrae.
Figure 3:
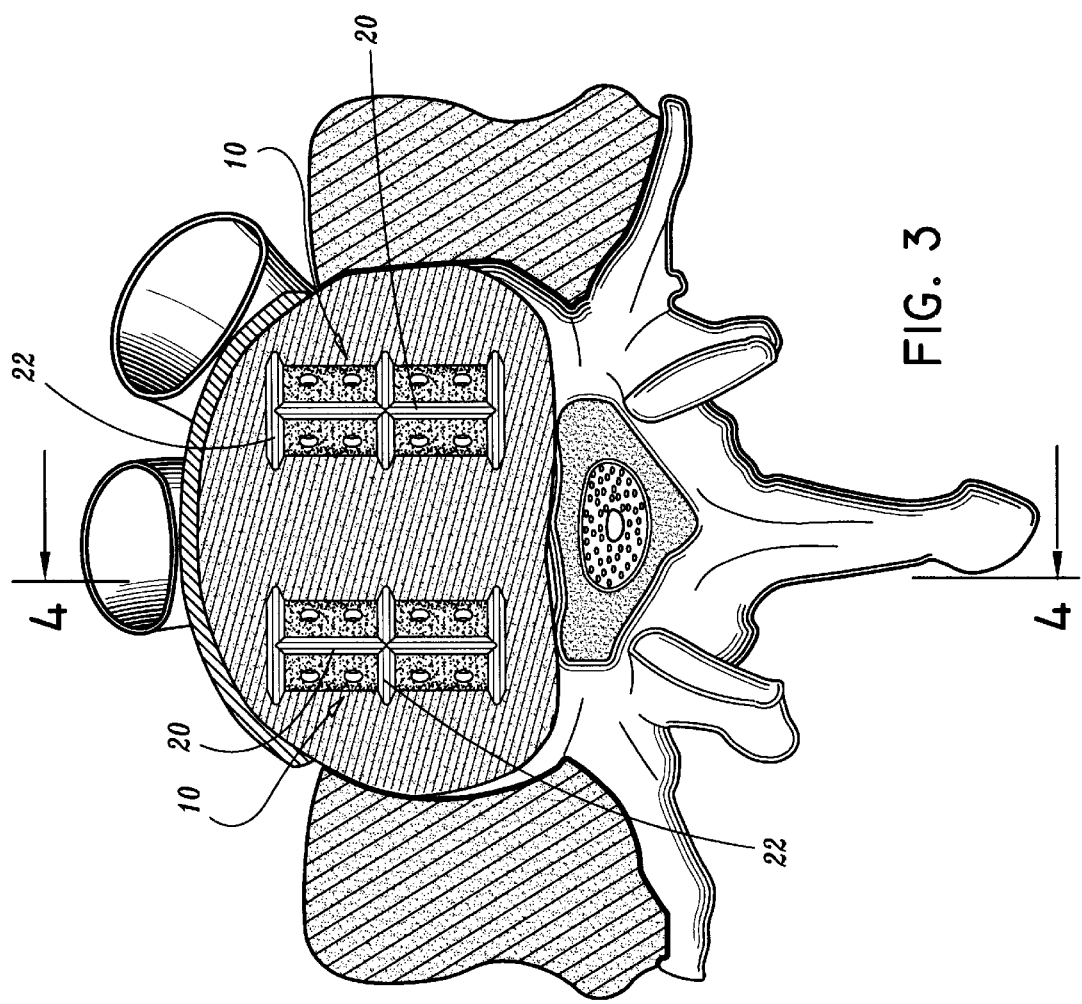
FIG. 3 is a sectional view of the vertebral column taken along the lines 3—3 of FIG. 2 illustrating insertion of a pair of the fusion implants of FIG. 1 within the intervertebral space.
Figure 4:
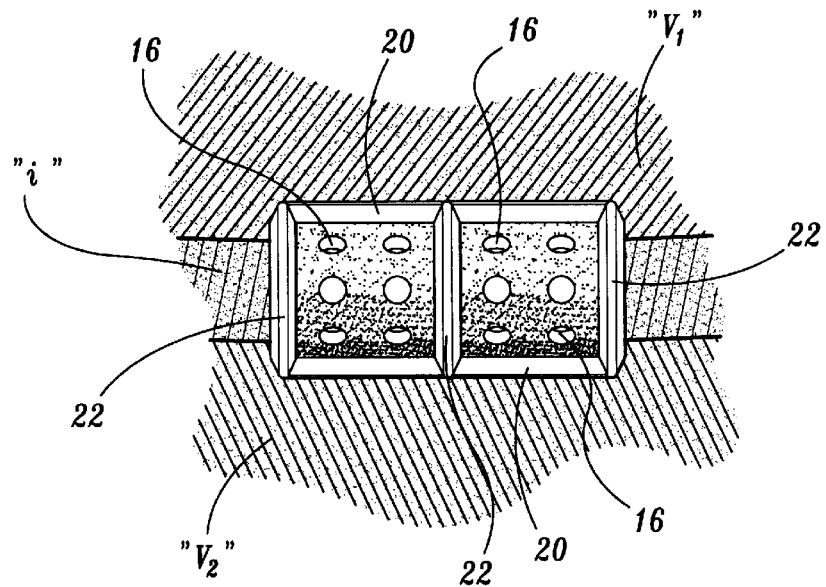
FIG. 4 is a sectional view taken along the lines 4—4 of FIG. 3 further illustrating insertion of the fusion implant within the intervertebral space.

With respect now to FIGS. 2–4, the intervertebral space "i" is accessed utilizing appropriate retractors to expose either the posterior or anterior vertebral surface depending on the desired approach. A discectomy may be performed to remove a portion or all of the diseased intervertebral space. Utilizing an orthopedic chisel or drill, a first bore is drilled in the adjacent vertebral "$V_1$, $V_2$" on one lateral side thereof to provide even purchase into the vertebral end plates. With the use of an insertion instrument or the like, fusion implant 10 is inserted into the drilled bore whereby upon insertion bioabsorbable implant member 12 and support structure 18 engages the adjacent vertebral portions. In the preferred method, implant 10 is positioned within the bore in a manner where axial support ribs 20 are in alignment with the vertebral column and in engagement with respective vertebral portions "$V_1$, $V_2$" as best depicted in FIG. 4.

Bone growth inducing substances are then gathered from, for example, the iliac crest as is conventional, and packed into the internal cavity 14 of implant member 12 until the member is completely filled. Alternatively, the bone growth inducing substances may be packed within internal cavity 14 of bioabsorbable implant member 12 prior to insertion of implant 10 within the drilled bore.

During the initial stages of healing, support structure 18 bears most of the compressive loads of the vertebral column while implant member 12 bears a smaller amount of load. Over time, bioabsorbable implant member 12 begins to degrade as the vertebral bone and bone graft material fuse, thereby shifting more of the load bearing away from support structure 18 and to the fused bony tissue communicating through the apertures 16 of implant member 12. Bioabsorbable implant member 12 is eventually fully absorbed within the body, thus leaving only support structure 18 within the intervertebral space.

Thus, the fusion implant 10 of the present disclosure adequately supports the adjacent vertebral portions "$V_1$, $V_2$" in spaced relation during all stages of the healing process. The supporting function of the bioabsorbable implant member 12 enables the use of a support structure 18 which occupies a minimal volume thus minimizing the amount of foreign implant material left in the vertebral column.

Figure 5:
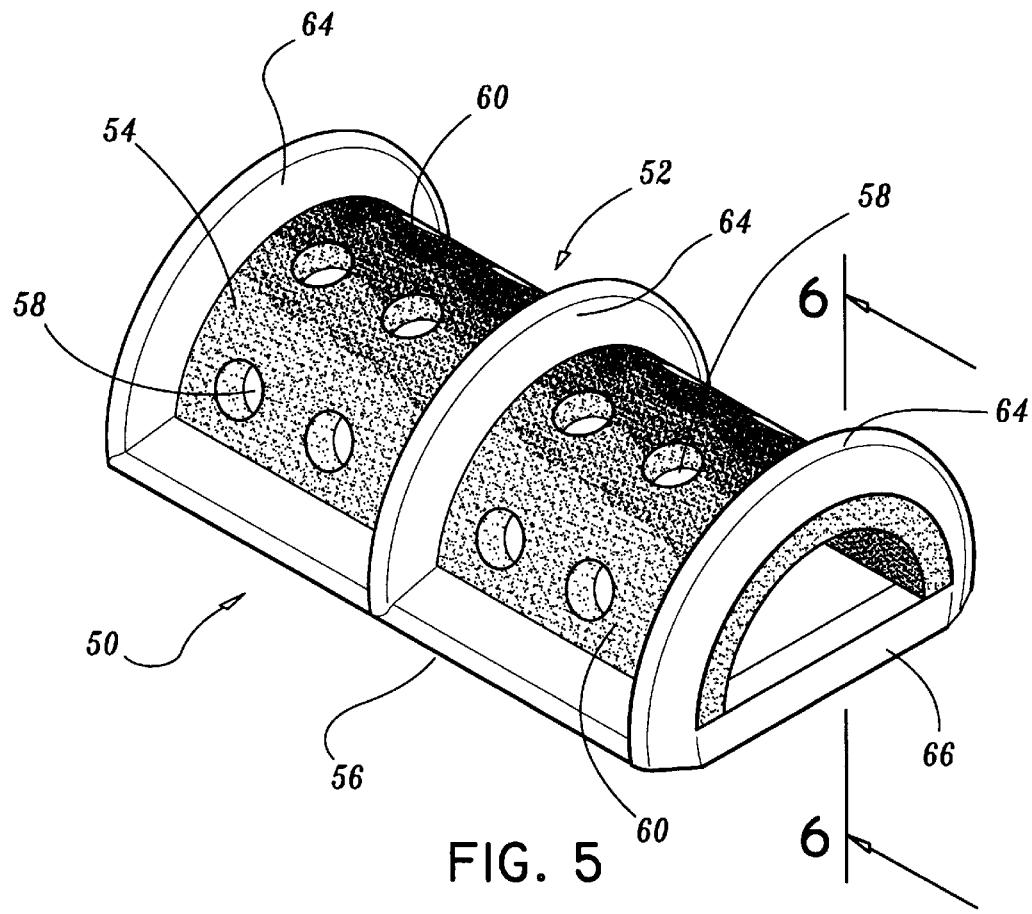
FIG. 5 is a perspective view of an alternate embodiment of the fusion implant of FIG. 1.
Figure 6:
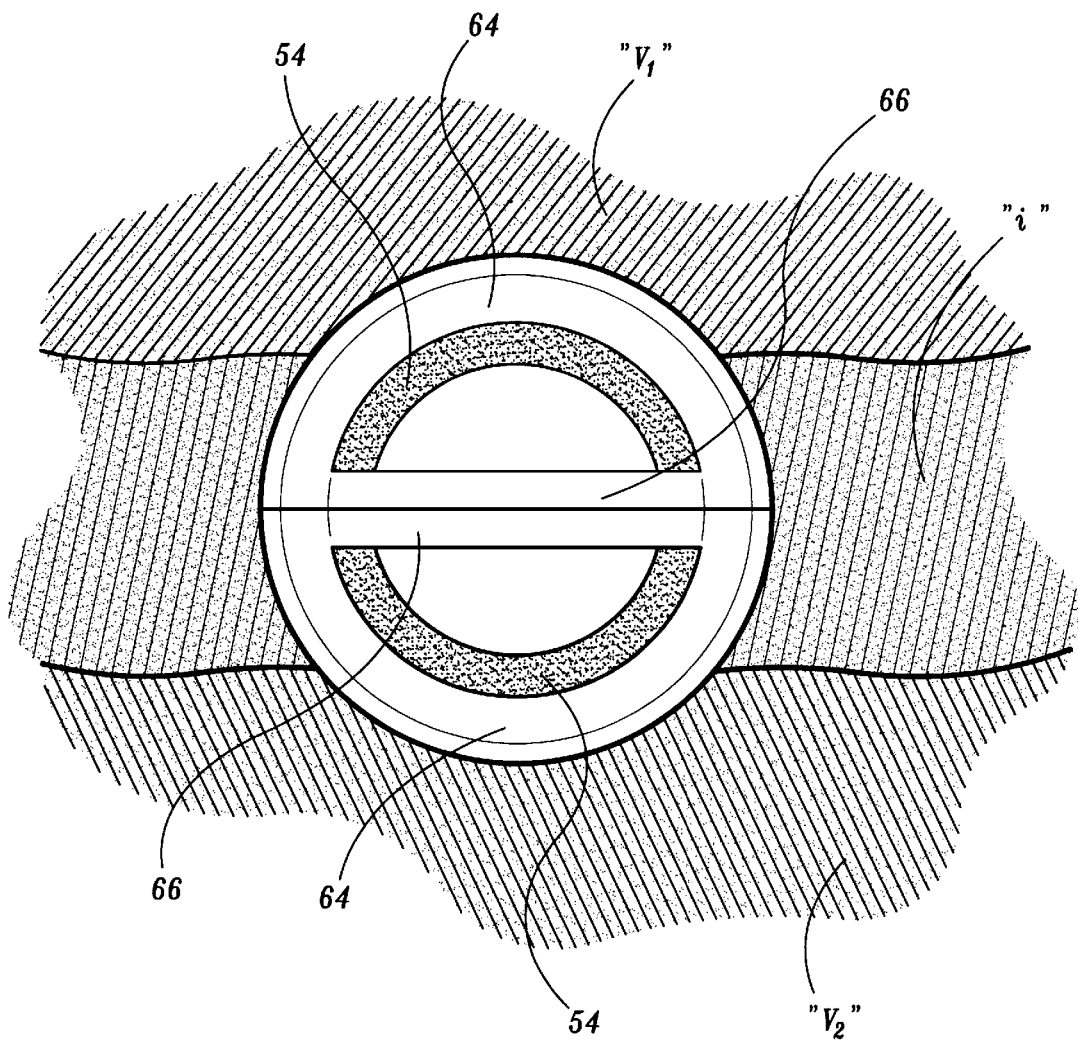
FIG. 6 is a sectional view of the vertebral column within the intervertebral space illustrating insertion of the fusion implant of FIG. 5.

Referring now to FIGS. 5–6, an alternate embodiment of the fusion implant 10 of the present disclosure is illustrated. Implant 50 is substantially similar to the implant 10 of FIG. 1, but, includes implant semi-circular half sections 52 which when assembled form the cylindrical implant depicted in FIG. 6. More particularly, each half section 52 includes bioabsorbable member 54 fabricated from any of the bioabsorbable materials identified above and support structure 56. Bioabsorbable member 54 defines a half-cylinder configuration and has a plurality of apertures 58 in its outer wall surface 60. Support structure 56 is a half cage configuration including first and second axial support ribs 62 connected by peripheral support ribs 64 and a pair of transverse support ribs 66 connecting the ends of the axial support ribs 62. In the preferred arrangement, bioabsorbable implant member 54 is positioned within support structure 56 as best depicted ion FIG. 5.

In the assembled condition of implant 50, the two implant half sections 52 are arranged in superposed relation with axial support ribs 56 and transverse support ribs 66 of respective half sections 52 in contacting relation. In one method of inserting implant 50 within the drilled bore, the implant half sections 52 may be assembled and then inserted within the drilled bore. Alternatively, one half section 52 may be positioned within the drilled bore followed by insertion of the second half section 52. Once disposed within the drilled bore, half sections 52 may be arranged as depicted in FIG. 6 in superposed relation with peripheral support ribs 64 of each half section 52 contacting the respective vertebral portions "$V_1$, $V_2$" and transverse ribs 66 in general parallel relation with the vertebral end plates.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A prosthetic implant apparatus for facilitating fusion of adjacent vertebral portions, comprising an implant member dimensioned to be at least partially positioned within an intervertebral space defined between adjacent vertebral portions, the implant member defining a longitudinal axis and having a cross-sectional dimension transverse to the longitudinal axis sufficient to at least span the intervertebral space, the implant member having an outer wall and an internal cavity defined within the outer wall for reception of bone growth inducing substances, the implant member comprising a bioabsorbable material and having a nonabsorbable cage structure associated therewith, the cage structure having sufficient rigidity to support and maintain the adjacent vertebral portions in spaced relation during healing, the cage structure including at least two axial rib portions and a plurality of peripheral rib portions connecting the axial rib portions.

2. The apparatus according to claim 1 wherein the bioabsorbable material is disposed within the support structure.

3. The apparatus according to claim 1 wherein the bioabsorbable material is arranged to define a substantially tubular member, the tubular member being at least partially disposed within the support structure, the tubular member defining the internal cavity and having apertures extending through an outer surface thereof in communication with the internal cavity.

4. A prosthetic implant apparatus for facilitating fusion of adjacent vertebral portions, comprising an implant member dimensioned to be at least partially positioned within an intervertebral space defined between adjacent vertebral portions, the implant member defining a cross-sectional dimension sufficient to at least span the intervertebral space such that opposed contacting surfaces thereof engage respective vertebral portions, the implant member including a first bioabsorbable member comprising a bioabsorbable material and a second substantially nonabsorbable rigid member, the first bioabsorbable member and the second rigid member cooperating to maintain the adjacent vertebral portions in spaced relation during healing and while the bioabsorbable material of the first bioabsorbable member is absorbed into tissue, the first bioabsorbable member being disposed within the second rigid member and being configured to define an outer wall having an internal cavity for reception of bone growth inducing substances.

5. The apparatus according to claim 4 wherein the bioabsorbable material is selected from the group consisting of polymers or copolymers of glycolide, lactide, troxanone, trimethylere carbonate and lactones.

6. The apparatus according to claim 4 wherein the first bioabsorbable member is fabricated solely from a bioabsorbable material.

7. The apparatus according to claim 4 wherein the second rigid member comprises a material selected from the group consisting of stainless steel, titanium, titanium alloys, aluminum, polymeric material and ceramic.

8. The apparatus according to claim 7 wherein the second rigid member is a cage body having an internal bore wherein the first bioabsorbable member is positioned within the internal bore and contained therein.

9. The apparatus according to claim 8 wherein the first bioabsorbable member is an enclosed member, the enclosed member having the outer wall which defines the internal cavity, the outer wall of the enclosed member including a plurality of apertures extending therethrough to permit communication with bone growth inducing substances within the internal cavity.

10. The apparatus according to claim 9 wherein the enclosed member is generally cylindrically-shaped.

11. The apparatus according to claim 10 wherein the implant member includes first and second implant sections, each implant section including the first bioabsorbable member and the second rigid member.

12. The apparatus according to claim 11 wherein each implant section defines a semi-circular cross-sectional dimension.

13. An apparatus for facilitating fusion of adjacent vertebral portions, comprising an implant member dimensioned to be at least partially positioned within an intervertebral space defined between adjacent vertebral portions, the implant member including a rigid cage member defining a longitudinal bore and a bioabsorbable member at least partially positioned within the bore of the cage member, the bioabsorbable member arranged to define an outer wall and having an internal chamber defined by the outer wall for accommodating bone growth inducing substances, and having a plurality of apertures extending through the outer wall in communication with the internal chamber to facilitate bone ingrowth, the cage member and the bioabsorbable member cooperating to maintain the adjacent vertebral portions in spaced relation during healing.

14. The apparatus according to claim 13 wherein the bioabsorbable member is arranged to define a substantially tubular-shaped member.

15. An apparatus for facilitating fusion of adjacent vertebral portions, comprising an implant member dimensioned to be at least partially positioned within an intervertebral space defined between adjacent vertebral portions and defining a longitudinal axis, the implant member including a pair of implant sections, each implant section including a rigid cage member and a bioabsorbable member at least partially positioned within the cage member, the implant sections assemblable with respect to each other to define an effective cross-sectional dimension transverse to the longitudinal axis sufficient to at least span the intervertebral space to maintain the adjacent vertebral portions in spaced relation during healing.

16. The apparatus according to claim 15 wherein the implant member is generally cylindrically-shaped.

17. The apparatus according to claim 16 wherein each cage member includes a pair of spaced longitudinal rib portions extending in a general longitudinal direction and at least two peripheral rib portions interconnecting the longitudinal rib portions.

18. The apparatus according to claim 17 wherein each implant section defines a semi-circular cross-sectional dimension.

* * * * *